United States Patent
Sawanoi et al.

(10) Patent No.: US 9,351,689 B2
(45) Date of Patent: May 31, 2016

(54) SPHYGMOMANOMETER HAVING FUNCTION OF CALCULATING RISK DEGREE OF CIRCULATORY SYSTEM DISEASE

(75) Inventors: Yukiya Sawanoi, Nara (JP); Kanako Saito, Kyoto (JP); Toshiaki Yuasa, Moriyama (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 1134 days.

(21) Appl. No.: 13/404,425

(22) Filed: Feb. 24, 2012

(65) Prior Publication Data
US 2012/0253208 A1 Oct. 4, 2012

(30) Foreign Application Priority Data
Mar. 28, 2011 (JP) ................. 2011-069927

(51) Int. Cl.
A61B 5/02 (2006.01)
A61B 5/00 (2006.01)
A61B 5/022 (2006.01)

(52) U.S. Cl.
CPC ........... *A61B 5/7275* (2013.01); *A61B 5/02225* (2013.01)

(58) Field of Classification Search
CPC ... A61B 5/02225; A61B 5/7275; A61B 5/022
USPC ................................. 600/490–499
See application file for complete search history.

(56) References Cited

U.S. PATENT DOCUMENTS 6,730,039 B2 * 5/2004 Nakagawa .................... 600/485
7,070,566 B2 * 7/2006 Medero et al. ................ 600/494
7,815,569 B2 * 10/2010 Kovatchev et al. ........... 600/365
8,951,192 B2 * 2/2015 Osorio ................. A61B 5/4094
  600/300
2002/0193691 A1 * 12/2002 Sato ................... A61B 5/02125
  600/495

(Continued)

FOREIGN PATENT DOCUMENTS

JP H06-14893 A 1/1994
JP 2002-102184 A 4/2002

(Continued)

OTHER PUBLICATIONS

Office Action issued in corresponding Japanese Patent Application No. 2011-069927 dated Mar. 17, 2015 (6 pages).

(Continued)

*Primary Examiner* — Navin Natnithithadha
(74) *Attorney, Agent, or Firm* — Osha Liang LLP

(57) ABSTRACT

An electronic sphygmomanometer having a function to calculate an index value of risk of circulatory system disease from measured blood pressure information includes a CPU, a memory, and a display. The CPU calculates the blood pressure of a person being examined based on pressure changes of an air bladder as measured by a pressure sensor. The memory stores data of the measured blood pressure together with time information of the measurement. The CPU calculates an index value of risk of circulatory system disease of the person being examined based on a difference between a blood pressure value obtained from a measurement and a blood pressure value obtained from a previous measurement and an elapsed time between the measurement and the previous measurement, A display part displays the calculated index value of risk of circulatory system disease of the person being examined together with the measured blood pressure.

8 Claims, 10 Drawing Sheets

(56) References Cited

U.S. PATENT DOCUMENTS

| | | | |
|---|---|---|---|
| 2003/0078508 A1* | 4/2003 | Nakagawa | 600/500 |
| 2004/0176692 A1 | 9/2004 | Kario et al. | |
| 2004/0181157 A1* | 9/2004 | Medero et al. | 600/500 |
| 2005/0228242 A1* | 10/2005 | Kawamura et al. | 600/300 |
| 2011/0251468 A1* | 10/2011 | Osorio | A61B 5/0476 600/300 |
| 2011/0306845 A1* | 12/2011 | Osorio | G06F 19/345 600/300 |
| 2011/0306846 A1* | 12/2011 | Osorio | A61B 5/4094 600/301 |

FOREIGN PATENT DOCUMENTS

| | | |
|---|---|---|
| JP | 2004-261452 A | 9/2004 |
| JP | 2005-218492 A | 8/2005 |
| JP | 2009-523512 A | 6/2009 |
| JP | 2009-233003 A | 10/2009 |

OTHER PUBLICATIONS

Office Action issued in corresponding Japanese Application No. 2011-069927 dated Sep. 24, 2014, and English translation thereof (7 pages).

Office Action in corresponding Chinese Patent application No. 201210090239.3 issued on Dec. 3, 2013 (14 pages).

Zhang; "Concepts of Blood Pressure Variability and Morning Blood Pressure Surge and Clinical Significances thereof"; Chin J. Cardiol, vol. 34, No. 3, pp. 287-288; Mar. 2006 (2 pages).

Patent Abstracts of Japan, Publication No. 2004-261452, publication date Sep. 24, 2004 (1 page).

Patent Abstracts of Japan, Publication No. 2005-218492, publication date Aug. 18, 2005 (1 page).

* cited by examiner

FIG. 6

| ID | Measurement date and time | User information | Blood pressure value/pulse rate | circulatory system risk |
|---|---|---|---|---|
| 1 | yy/mm/dd hh:mm1 | USER A | SYSinf, DIAinf, PLSinf | — |
| 2 | yy/mm/dd hh:mm2 | USER B | SYSdef, DIAdef, PLSdef | ΔSYS, ΔDIA |
| . | . | . | . | . |
| . | . | . | . | . |
| . | . | . | . | . |
| . | . | . | . | . |
| . | . | . | . | . |

FIG. 11

| No | DATE | TIME | SBP | DBP | PLS |
|---|---|---|---|---|---|
| Inf. | 2009/2/9 | 11:27 | 162 | 98 | 92 |
| Def. | 2009/2/9 | 11:28 | 150 | 89 | 91 |
| AVG | | | 156 | 94 | 91 |
| r | | | 12 | 9 | |

SPHYGMOMANOMETER HAVING FUNCTION OF CALCULATING RISK DEGREE OF CIRCULATORY SYSTEM DISEASE

BACKGROUND OF INVENTION

This invention relates to an electronic sphygmomanometer and calculation program, and particularly, it relates to an electronic sphygmomanometer and calculation program that calculates an index value of risk of circulatory system disease based on the blood pressure value.

Blood pressure is one index to analyze circulatory system disease, and blood pressure is effective in analyzing the risk of circulatory system disease to prevent circulatory system diseases, such as, stroke, heart failure, heart attack, and the like. Especially, morning high blood pressure where the blood pressure increases in the morning is related to heart disease, strokes, and the like. Moreover, even among morning blood pressures, a symptom where the blood pressure dramatically increases between one hour to one hour and a half after waking referred to as "morning surge" has been shown to have a causal relationship to strokes. In other words, it can be said that understanding the mutual relationship between time (life style) and blood pressure fluctuation is effective for risk analysis for circulatory system disease.

By focusing on this point; various sphygmomanometers to analyze risk of cardiovascular system diseases are suggested. For example, Publication of Japanese Unexamined Patent Application 2004-261452 discloses a technique to calculate a risk of circulatory system disease according to a difference in, or an average of, blood pressure values measured during a predetermined time period such as morning or evening.

SUMMARY OF INVENTION

The method disclosed in the above mentioned patent application reference is a method to calculate risk based on blood pressure fluctuations during a day. However; blood pressure not only fluctuates during a day but also fluctuates during short periods of time of 10 minutes or less. This is considered to be dependent upon an adjustment mechanism of the circulatory system.

Therefore, one or more embodiments of the present invention provide an electronic sphygmomanometer and calculation program that can calculate an index value of risk of circulatory system disease based on the dynamics of adjustment mechanisms of the circulatory system.

One or more embodiments of the present invention provide an electronic sphygmomanometer having a function to calculate an index value of risk of circulatory system disease from measured blood pressure information. The electronic sphygmomanometer comprises: means for measuring blood pressure of a person being examined; a memory for storing data of measured blood pressure of the person being examined together with a time information of the measurement means for calculating an index value of risk of circulatory system disease of the person being examined based on a difference between a blood pressure value of the person being examined obtained from a measurement and a blood pressure value of the person being examined obtained from a previous measurement and elapsed time between the measurement and the previous measurement; and means for displaying the calculated index value of risk of circulatory system disease of the person being examined together with the measured blood pressure.

According to one or more embodiments of the present invention, the index value of risk of circulatory system disease is calculated by dividing the difference between a blood pressure value of the person being examined obtained from a measurement and a blood pressure value of the person being examined obtained from a previous measurement by the elapsed time between the measurement and the previous measurement.

According to one or more embodiments of the present invention, the blood pressure value of the person being examined is systolic blood pressure obtained from each measurement.

The electronic sphygmomanometer according to one or more embodiments of the present invention further comprises means to measure the blood pressure of the person being examined at an inflating process of an air bladder of a cuff and means to measure the blood pressure of the person being examined at a deflating process of the cuff that follows after the inflating process. An index value of risk of circulatory system disease of the person being examined is calculated by dividing the difference of the blood pressure value obtained from the measurement at the inflating process and the blood pressure value obtained from the measurement at the deflating process by the elapsed time between the measurement at the inflating process and the measurement at the deflating process.

According to one or more embodiments of the present invention, the electronic sphygmomanometer further includes means to input ID information to specify the person being measured.

The electronic sphygmomanometer according to one or more embodiments of the present invention further comprises means to input II) information of the person being examined.

One or more embodiments of the present invention are a computer program for calculating an index value of risk of circulatory system disease of the person being examined. The program comprises: a step of measuring the blood pressure of a person being examined based on a change of internal pressure of a fluid bladder of a sphygmomanometer, a step of storing data of measured blood pressure of the person being examined together with time information of the measurement in a memory; a step of retrieving data of blood pressure of the person being examined obtained from a previous measurement and stored in the memory together with time information of the previous measurement; and a step of calculating an index value of risk of circulatory system disease of the person being measured by dividing the difference between the blood pressure value of the person being examined obtained from the measurement and the blood pressure value of the person being examined obtained from the previous measurement by elapsed time between the measurement and the previous measurement.

According to one or more embodiments of the present invention, the blood pressure value of the person being examined is systolic blood pressure obtained from each measurement.

One or more embodiments of the present invention are a method of calculating index value of risk of circulatory system disease from blood pressure information. The method comprises: measuring blood pressure of a person being examined; retrieving data of blood pressure value of the same person measured by a previous measurement and stored in a memory; and dividing a difference between a blood pressure value of the person being examined obtained from the measurement and a blood pressure value of the same person obtained from a previous measurement by elapsed time between the measurement and the previous measurement to obtain index value of risk of circulatory system disease.

According to one or more embodiments of the present invention, the index value of risk of circulatory system disease can be easily calculated based on the dynamics of adjustment mechanisms of the circulatory system.

BRIEF DESCRIPTION OF THE DRAWINGS

FIG. 6 exemplifies a detailed example of measurement results that are stored in a predetermined region of memory.

FIG. 11 shows a screen example.

DETAILED DESCRIPTION OF INVENTION

Embodiments of the present invention are explained hereinafter with reference to drawings. In the explanation given below, the same reference number is applied to the same part and configuration element. The names and functions thereof are the same.

It is known that for the fluctuation of blood pressure, the intervals at which the fluctuations occur and the degree of fluctuation direr depending on the cause of the occurrence. This is for example, disclosed in "Measurement Method and Clinical Evaluation of Blood Pressure" authored by Osamu Tochikubo (published by the Medical Tribune).

Specifically, the shortest blood pressure fluctuation is a fluctuation that is normally 0 to 4 mmHg for a fluctuation of 1 beat to 1 beat (blood pressure fluctuation in the first order); however, drops of from several mmHg to 10 mm Hg or more have been observed in patients with myocardial disorders.

The next shortest blood pressure fluctuation is respiratory blood pressure fluctuation (blood pressure fluctuation in the second order), and this is a fluctuation in which the blood pressure slightly rises at the time of inspiration, and the blood pressure slightly lowers at the time of expiration, and of course, this fluctuation may be prominent depending on the disease.

In addition, there is a blood fluctuation that occurs in cycles of 10-60 seconds (blood pressure fluctuation in the third order). Particularly, this can be commonly seen under conditions of when standing at the time of an exercise load, when a drug is given, and the like.

In addition to these blood pressure fluctuations, the blood pressure can largely fluctuate due to environmental factors such as stress. These blood pressure fluctuations are based on adjustment mechanisms of the circulatory system.

Figure 1:
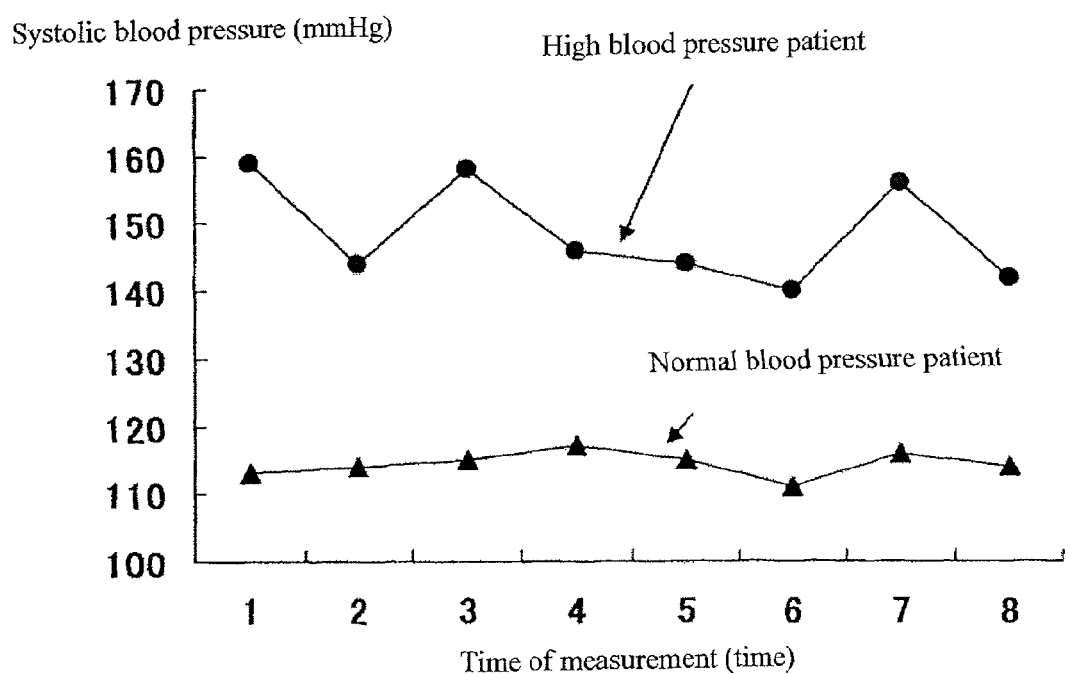
FIG. 1 is a chart indicating fluctuations in blood measurement results between a high blood pressure patient and a patient with a normal blood pressure.

Measurements taken by the inventors of embodiments of the present invention reveal that high blood pressure patients especially have larger blood pressure value fluctuations in a short period of time compared to patients with normal blood pressure values. FIG. 1 shows fluctuations of the blood pressure measuring results between the high blood pressure patients and the normal blood pressure patients, and it shows the results obtained by the inventors of embodiments of the present invention by measuring the blood pressure of the high blood pressure patients and normal blood pressure patients per every one minute interval. As is evident from FIG. 1, the high blood pressure patients have larger fluctuations in short periods of time compared to the normal blood pressure patients.

As related art, for example, in Publication of Japanese Unexamined Patent Application 2005-218492, the applicants of this application disclose a technique to evaluate the risk of circulatory system disease based on the fluctuations of the blood pressure value for a long period of time, for example, for a week or a month. It also became clear that this kind of long period of time of blood pressure fluctuation also has a very close relationship with the risk of circulatory system disease, and its effectiveness is made evident even in the guidelines of scientific society.

However, with a patient who has a high risk of circulatory system disease, blood pressure fluctuations may occur at, for example, 10 mmHg or higher within short intervals of about 10 minutes or less.

Accordingly the inventors of embodiments of the present invention considered that it is possible to understand the dynamics of adjustment mechanisms of the circulatory system by understanding the blood pressure fluctuations that occur within a short period of time, for example, within 10 minutes or 5 minutes. Accordingly, in one or more embodiments of the present invention, the index value of risk of circulatory system disease is calculated based on the fluctuations of the blood pressure values that are shown as measurement results obtained in a short period offline.

The fluctuation of the blood pressure value within a short period of time is shown in the ratio to elapsed time t that is the fluctuation degree between the blood pressure value of the first timing and the second timing after the predetermined period t2. This fluctuation degree is applicable to, for example, the difference between the systolic blood pressure SBP1 at the first timing and the systolic blood pressure SBP2 at the second timing and to the ratio between the systolic blood pressure value SBP1 at the first timing and the systolic blood pressure value SBP2 at the second timing. Accordingly, one or more embodiments of the present invention use the value that expresses the fluctuation of the blood pressure value obtained as stated above as an index value of risk of circulatory system disease.

Figure 2:
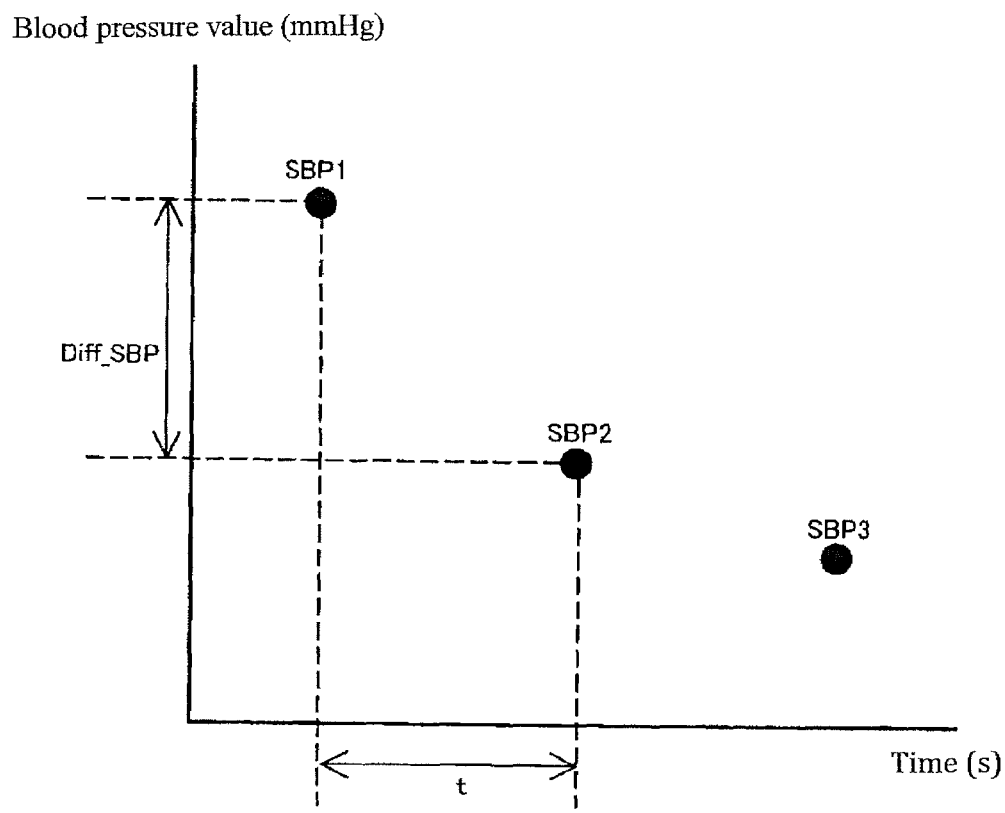
FIG. 2 is a chart for explaining one example of an index value of risk of circulatory system disease.

FIG. 2 explains one example of an index value of risk of circulatory system disease. Referring to FIG. 2, as one example, the value that is obtained by dividing the difference, Diff_SBP, between the systolic blood pressure value SBP1 and the systolic blood pressure value SBP2 can be used for the index value of risk of circulatory system disease, by the elapsed time t. The systolic blood pressure value is used as the blood pressure value obtained by the measurement in the explanation hereafter, however, the used value is not limited to the systolic blood pressure value, and can be the diastolic blood pressure, or can be the average blood pressure, pulse pressure, or a combination of both.

Moreover, the systolic blood pressure value can be a combination with the pulse rate measured at the same time with the blood pressure. The blood pressure is determined by the blood volume (cardiac output) that is output by the heart. In other words, increasing the blood pressure can be done by either one of increasing the cardiac output per heartbeat, or by increasing the cardiac output per unit time by increasing the heart rate. When the blood pressure is increased in the condition when the pulse rate is low, it means that the cardiac output per heartbeat is increased, and therefore, the load to the heart increases.

Figure 3:
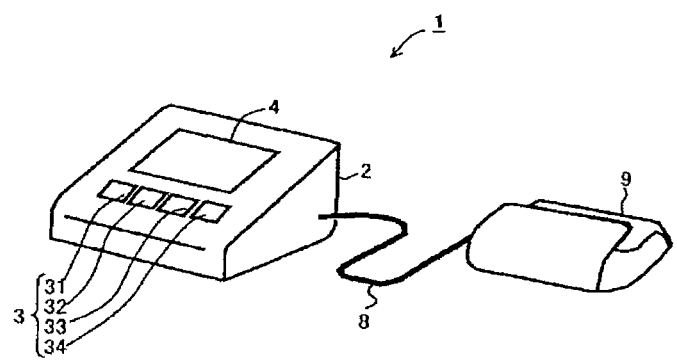
FIG. 3 illustrates a detailed example of an appearance of an electronic sphygmomanometer (hereinafter abbreviated as sphygmomanometer) according to the present embodiment.

FIG. 3 shows a detailed example of the appearance of the electronic sphygmomanometer 1 (herein after abbreviated as sphygmomanometer) of the present embodiment.

Referring to FIG. 3, the sphygmomanometer 1 includes a substrate 2 and an arm band 9 that is connected to the substrate 2 via an air tube 8 and is to install on the upper arm, which is a measurement part.

On the front part of the substrate 2, a display part 4 for displaying various information including measurement results and an operation part 3 that is operated in order to give various orders with respect to the sphygmomanometer 1 are arranged. The operation part 3 includes a switch 31 that is operated in order to turn on or off power, a switch 32 that is operated in order to give an order to start the measurement; a switch 33 that is operated to stop a measurement operation, and a switch 34 to be operated in order to call up the recorded information.

Figure 4:
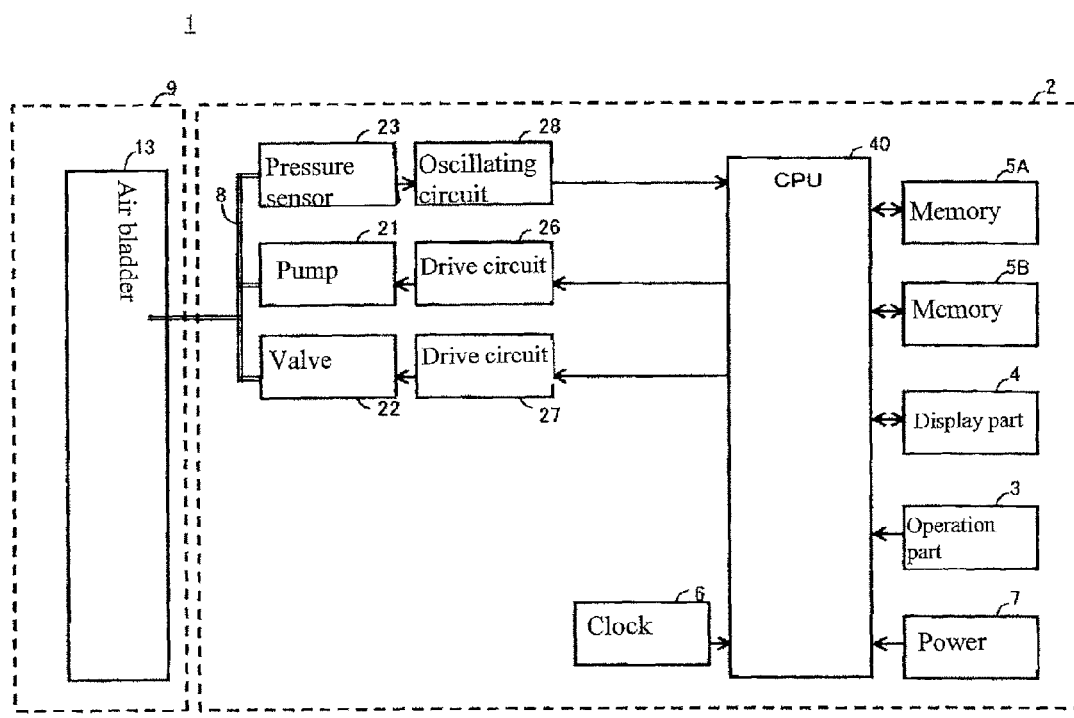
FIG. 4 is a block diagram illustrating a detailed example of a configuration of a sphygmomanometer.

FIG. 4 is a block diagram illustrating a detailed example of the configuration of the sphygmomanometer 1. Referring to FIG. 4, the arm band 9 includes an air bladder 13. The substrate 2 of the sphygmomanometer 1 includes a pressure sensor 23, a pump 21 and a valve 22 that are connected to the air bladder 13 via the air tube 8.

The pressure sensor is connected to an oscillating circuit 28. The pump 21 is connected to a drive circuit 26, and the valve 22 is connected to the drive circuit 27.

The drive circuit 26, the drive circuit 27 and the oscillating circuit 28 are connected to a Central Processing Unit (CPU) 40 for controlling the entire sphygmomanometer 1. Further, a clock 6, a display part 4, the operation part 3, as well as a memory 5A for processing and memory 5B for storing data, and the power 7 for supplying power are connected to the CPU 40.

The memory 5A becomes an operation area when CPU 40 executes programs. The memory 5B stores the control program that is executed by CPU 40 or the measurement value that is described later.

CPU 40 executes a predetermined program that is stored in the memory 5B based on the operation signal that is input from the operation part 3, and outputs the control signal to the drive circuit 26 and the drive circuit 27. The drive circuit 26 and the drive circuit 27 drive the pump 21 and the valve 22, respectively, according to the control signal.

The pump 21 injects air into the air bladder 13 by the drive that is controlled by the drive circuit 26 according to the control signal from CPU 40. The valve 22 exhausts the air in the air bladder 13 when opening and closing of the valve 22 is controlled by the drive circuit 27 according to the control signal from CPU 40.

The pressure sensor 23 is an electrostatic capacity type pressure sensor, and the capacity value fluctuates depending on the internal pressure fluctuation of the air bladder 13. The oscillating circuit 28 outputs the oscillating frequency signal depending on the capacity value of the pressure sensor 23, and inputs into CPU 40.

CPU 40 executes the predetermined processing based on the internal pressure fluctuation of the air bladder 13 that is obtained from the pressure sensor 23, and outputs the control signal to the drive circuit 26 and the drive circuit 27 depending on the result. Moreover, CPU 40 calculates the blood pressure value based on the internal pressure change of the air bladder 13 that is obtained by the pressure sensor 23, and outputs the data and the control signal to the display part 4 in order to perform the processing to display the measurement result on the display part 4. Moreover, CPU 40 performs the processing to store the measurement result to the memory 5B.

The arm band 9 is used for winding on an upper arm, which is a measurement portion at the tune of measurement. In that condition, the measurement operation is started when the switch 32 is pressed.

First Embodiment

Figure 5:
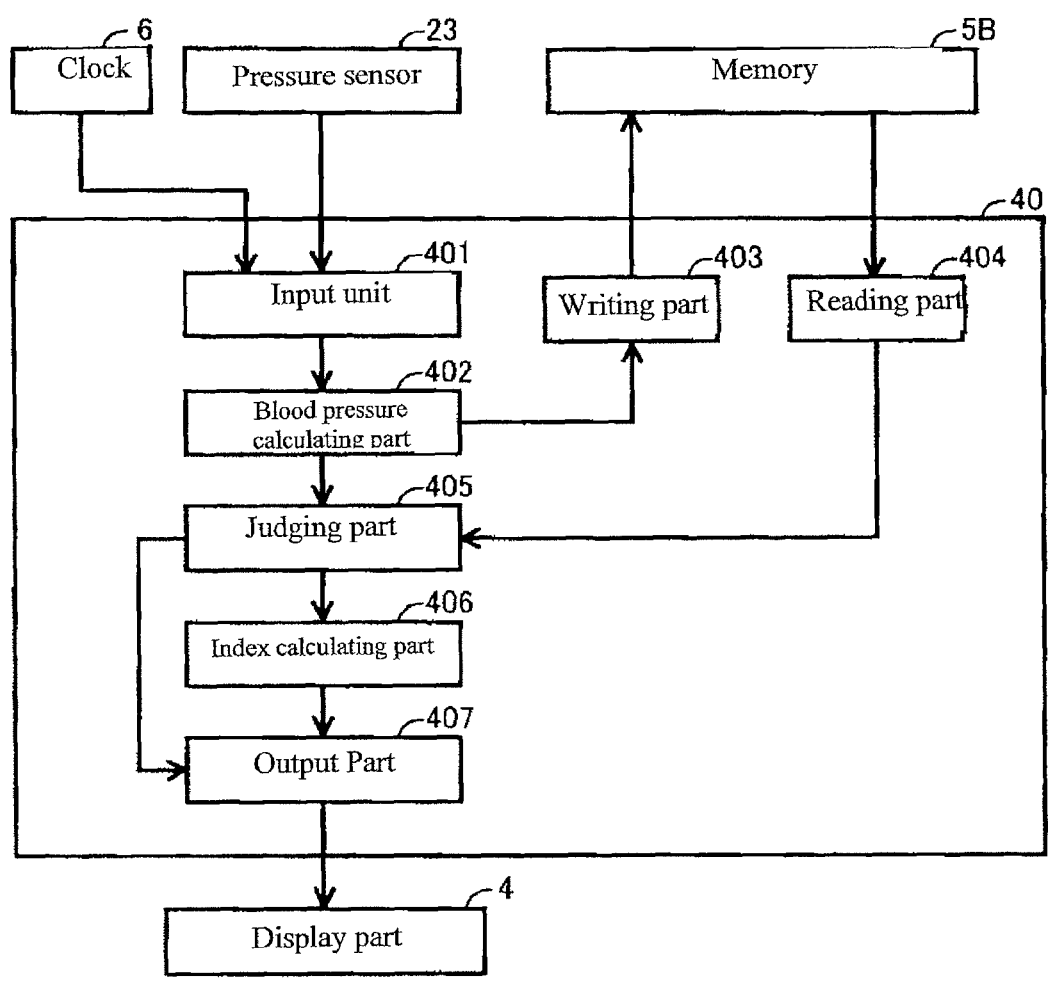
FIG. 5 is a block diagram illustrating a detailed example of a functional configuration of the sphygmomanometer according to the first embodiment.

FIG. 5 is a block diagram illustrating a detailed example of the functional configuration of the sphygmomanometer 1 of the first embodiment. Each function of FIG. 5 is mainly formed on CPU 40 by CPU 40 to read and execute the program stored in the memory 5B according to the operation signal from the operation part 3. At least one part may be formed as a hardware configuration as shown in FIG. 4.

Referring to FIG. 5, CPU 40 includes an input part 401 for receiving input from the sensor signal from the pressure sensor 23 and a date and time information from the clock 6, a blood pressure calculating part 402 for calculating the blood pressure value of the person being measured based on the pressure value shown by the sensor signal, a writing part 403 for writing the calculated blood pressure value as a measuring result together with the information specifying the measured date and time on the predetermined region of the memory 5B, a reading part 404 for reading the measurement result from the predetermined region of the memory 5B, a judging part 405 for judging whether or not to calculate the index value of risk of the circulatory system disease by comparing the measurement result obtained by calculating and the measurement result that is read, the index value calculating part 406 for calculating the index value of risk of the circulatory system disease by using the measurement result depending on the judging result made at the judging part 405, and an output part 407 for executing a processing to output the output at the display part 4 depending on the calculated index value or the judgment made not to calculate at the judging part 405.

FIG. 6 shows the detailed example of the measuring result that is stored in the predetermined region of the memory 5B. Referring to FIG. 6, at the predetermined region of the memory 5B, the blood pressure t value that is calculated at the blood pressure calculating part 402 is stored together with information specifying the measuring date and time. According to one or more embodiments of the present invention, the operation part 3 includes a button to specify the person being measured that is not shown in the operation part 3, and receives an order to specify the person being measured at the time of measurement, and the measurement result is stored with the information to identify the person being measured (user information). Accordingly, when there are several people being measured using the sphygmomanometer 1, the measurement result can be managed per the person being measured, and the index value of risk of the circulatory system disease can be calculated per the person being measured.

Further, as the measurement result, the index value (circulatory system risk) of risk of the circulatory system disease that is calculated by using the measurement result can be stored.

As stated above, the sphygmomanometer 1 performs several times of measurements within a certain degree of short period of time, and calculates the index value of risk of the circulatory system disease by using that result. Moreover; several times of measurement at this point include both the concept of when several bores of measurement is performed immediately before within the predetermined period of time that is a short period of time and when several times of the measurement is performed within the predetermined period that is a short period of time, respectively. Hence, when the blood pressure value is calculated at the blood pressure calculating part 402 based on the sensor signal 401 that is received at the input part 401, CPU 40 calculates the index value of risk of the circulatory system disease using the blood pressure value when the blood pressure value that is measured within the above-stated certain short period of time during blood pressure measurement is stored in the memory 5B. When this kind of blood pressure value is not stored in the memory 5B, the index value is not calculated.

Accordingly the reading part 404 reads the latest measurement result from the memory 5B when notified that the blood pressure value is calculated at that blood pressure calculating part 402, and inputs into the judging part 405. The judging part 405, by judging whether or not the measuring date and time of the input blood pressure that is input by the memory 5B is within the certain degree of short period of time from the measuring date and time of the blood pressure that is calculated at the blood pressure calculating part 402, judges whether or not to calculate the index value of risk of the circulatory system disease by using these blood pressure values.

Moreover, the certain degree of short period of time is not limited to a specified period; however; according to one or more embodiments of the present invention, this period of time is approximately 5 minutes. Hence, the explanation below uses a measurement value that is within 5 minutes.

Figure 7:
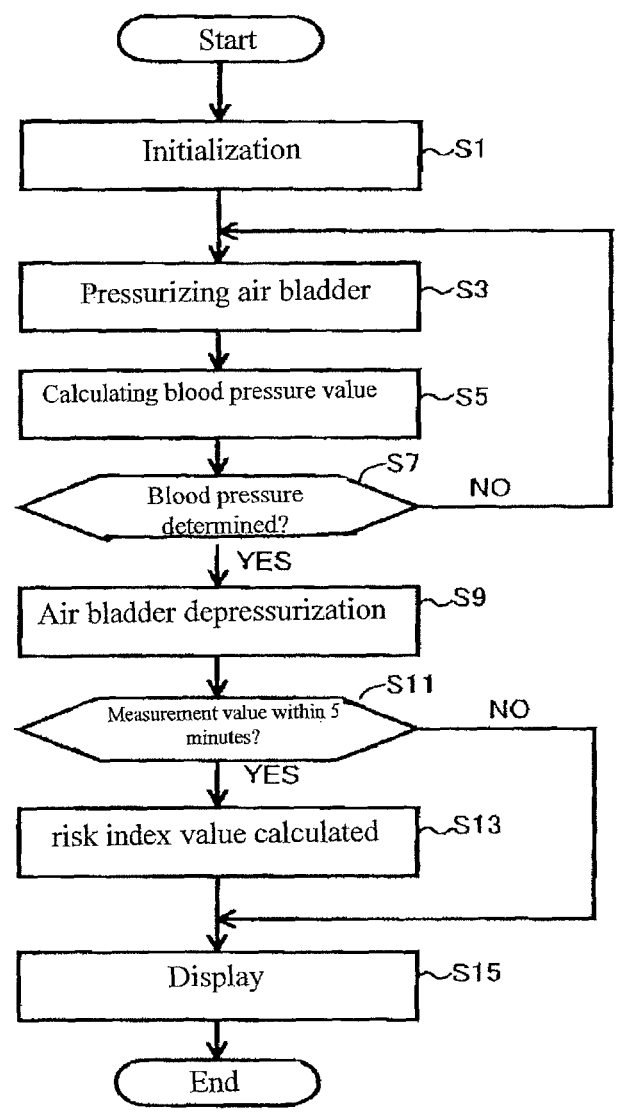
FIG. 7 is a flow chart that illustrates an operation in the sphygmomanometer according to the first embodiment.

FIG. 7 is a flow chart showing the operation on the sphygmomanometer 1 of the first embodiment. The operation shown in the flow chart of FIG. 7 is started by pressing the switch 32 that is included in the operation part 3. This operation can be realized by controlling each portion that is shown in FIG. 5 by CPU 40 to read the control program stored in the memory 5B.

Referring to FIG. 7, when the measurement operation is started, after CPU 40 initializes each part at Step S1, at Step S3, CPU 40 outputs the control signal with respect to the drive circuit 26 and the drive circuit 27, and closes the valve 22, operates the pump 21, and pressurizes (inflates) the air bladder 13.

At the process of pressurizing at Step S5, CPU 40 extracts the vibrational component in accordance with the volume of artery fluctuation that is convoluted by the internal pressure of the air bladder 13, and calculates the blood pressure value by the predetermined calculation. The calculation method of the blood pressure value at this point can be the calculation method of an oscillometric method adopted by a regular electronic sphygmomanometer.

Moreover, in this example, the blood pressure value is calculated based on the internal pressure fluctuation of the air bladder 13 during the pressurization process; however, the blood pressure can be calculated based on the internal pressure of the air bladder 13 in the depressurization (deflation) process.

When the calculation of blood pressure value is completed, and the blood pressure value is determined (YES at Step S7), at Step S9, CPU 40 stops pressurizing by outputting the control signal to the drive circuit 26, and furthermore, outputs the control signal to the drive circuit 27 and releases the valve 22. Thus, the air bladder 13 rapidly depressurizes.

Here, when the blood pressure value as the measurement result within 5 minutes from this measurement is stored at a predetermined region of memory 5B, (Yes at Step S11), at Step S13, CPU 40 calculates the index value r of risk of the circulatory system disease using the blood pressure value that is calculated at the above mentioned Step S5 and the above mentioned blood pressure that is stored at the memory 5B. Here, for example, the systolic blood pressure value, SBP1, that is measured first and the systolic blood pressure value, SBP2, that is measured later; and the measurement time interval t are used and calculated as shown in the equation 1 hereafter.

$$r=(SBP1-SBP2)/t \qquad \text{Equation (1)}.$$

Moreover; without being limited to the difference of the blood pressure values, r can be calculated as the equation (2) hereafter by using its ratio.

$$r=(SBP1/SBP2)/t \qquad \text{Equation (2)}.$$

Further; the above equations (1) and (2) are used to calculate the index value from the difference or ratio between the systolic blood pressure value, SBP1, that is measured at the first measurement and the systolic blood pressure value, SBP2, that is measured at the second measurement. However, this method is one example, and another method can be adopted. For example, according to one or more embodiments of the present invention, the index value may be calculated by the difference or the ratio between the systolic blood pressure value, SBP2, that is measured at the second measurement and the systolic blood pressure value, SBP3, that is measured at the third measurement and the representative value of several index values (such as average value, maximum value, minimum value or medium) may be outputted as the final index value. Moreover, according to one or more embodiments of the present invention, the difference or ratio of the several index values may be calculated, and that value may be determined as the final index value and output.

Subsequently, at Step S15, CPU 40 executes the processing to display the index value r of risk of the circulatory system disease that is calculated at Step S13 with the blood pressure value that is measured at Step S5 on the display part 4 as a measurement result, and completes a series of measurement operation.

Figure 8:
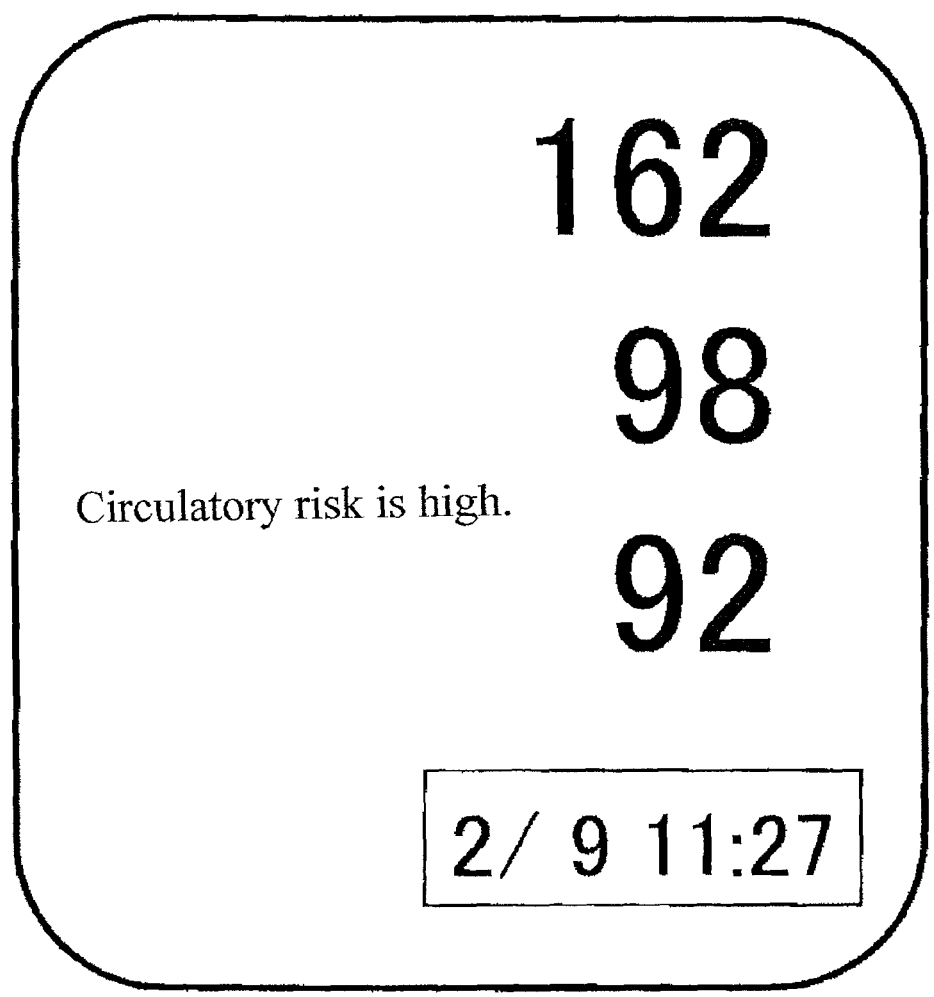
FIG. 8 shows a screen example.

FIG. 8 shows the screen example that is displayed on the display part 4 according to the processing at the above mentioned Step S15. As shown in FIG. 8, when the measurement is completed, the index value of risk of the circulatory system disease, which is calculated by using the blood pressure value that is obtained by the measurement, and also the blood pressure value that is measured immediately before, is displayed. Furthermore, according to one or more embodiments of the present invention, a threshold value concerning the index value may be stored in advance, and the comparison result may be displayed together with the blood pressure value by comparing the threshold value and the calculated index value. Moreover, in an example of FIG. 8, because the calculated index value is larger than the above mentioned threshold value, the pre-stored message "circulatory system risk is high" is displayed together with the blood pressure value depending on its comparison result.

Moreover; in the flow chart shown in FIG. 7, when the blood pressure value as the measurement result that is measured within 5 minutes from this measurement is not stored in the predetermined region of the memory 5B, the calculation of the index value of the above mentioned Step S13 is not performed. In this case, at the above mentioned Step S15, only the blood pressure value that is measured at the above mentioned Step S5 can be displayed. Moreover, in order to make calculation of the index value possible, for example, a message such as "please measure once again within 5 minutes" is stored in advance, and the message can be displayed together with the blood pressure value that is measured at the above mentioned Step S5. By doing this the index value can be calculated by using this time's measurement result at the measurement time.

When the above mentioned operation is performed on the sphygmomanometer 1 of the first embodiment, it becomes possible to understand the dynamics of the adjustment mechanism of the circulatory system with a simple measurement. Further, the index value of risk of the circulatory system disease based on this can be known, and the risk of the circulatory system disease can be easily understood.

Second Embodiment

In the first embodiment, the blood pressure is measured in either one of the processes of the pressurization process or the depressurization process. Therefore, in order to obtain the several times of measurement result within the predetermined period, the user needs to perform the order to start the measurement for several times, and to execute the corresponding measurement operation.

Then, the sphygmomanometer 1 of the second embodiment measures the blood pressure during both the pressurization process and the depressurization process, each corresponding to the order of first measurement start, and calculates the index value of risk of the circulatory system disease.

Figure 9:
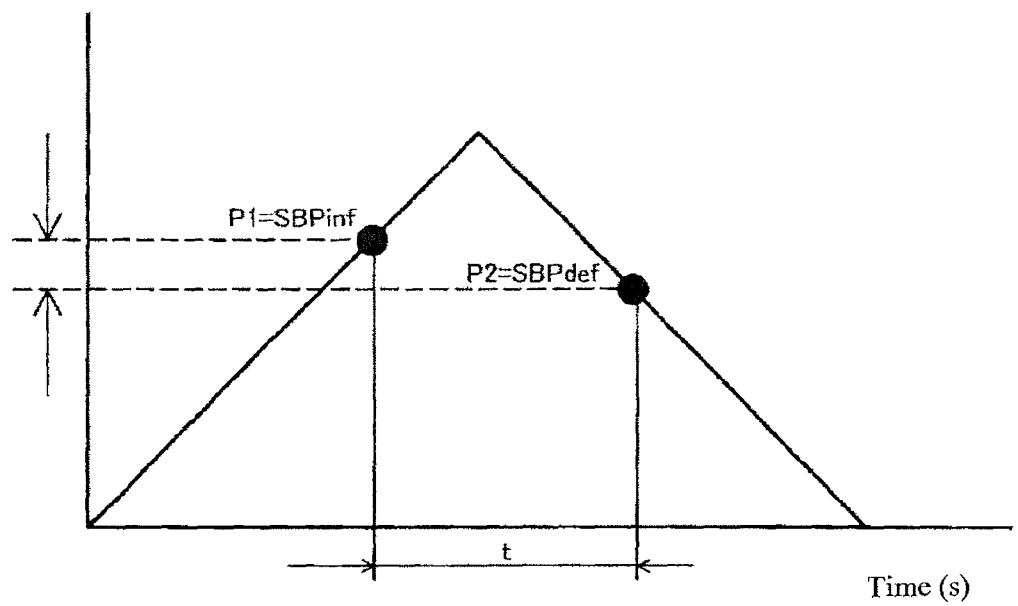
FIG. 9 is a chart for explaining a calculation method of an index value of risk of circulatory system disease by the sphygmomanometer according to the second embodiment.

FIG. 9 explains the calculating method of the index value of risk of the circulatory system disease of the sphygmomanometer 1 of the second embodiment Referring to FIG. 9, the sphygmomanometer 1 of the second embodiment calculates the difference (or its ratio) between the systolic blood pressure value, SBPinf, which is obtained by calculating the blood pressure value during the pressurization process, and the systolic blood pressure value, SBPdef which is obtained by calculating the blood pressure value during the depressurization process, and the value is used as the index value of risk of the circulatory system disease.

The functional configuration of the sphygmomanometer 1 of the second embodiment is approximately the same as the functional configuration of the sphygmomanometer 1 of the first embodiment shown in FIG. 5.

In the case of the sphygmomanometer 1 of the second embodiment, the judging part 405 at the blood pressure calculating part 402, judges whether or not it is possible to calculate the index value corresponding to whether or not the blood pressure value is calculated based on the sensor signal at the pressurization process when the blood pressure is calculated based on the sensor signal during the pressurization process.

Figure 10:
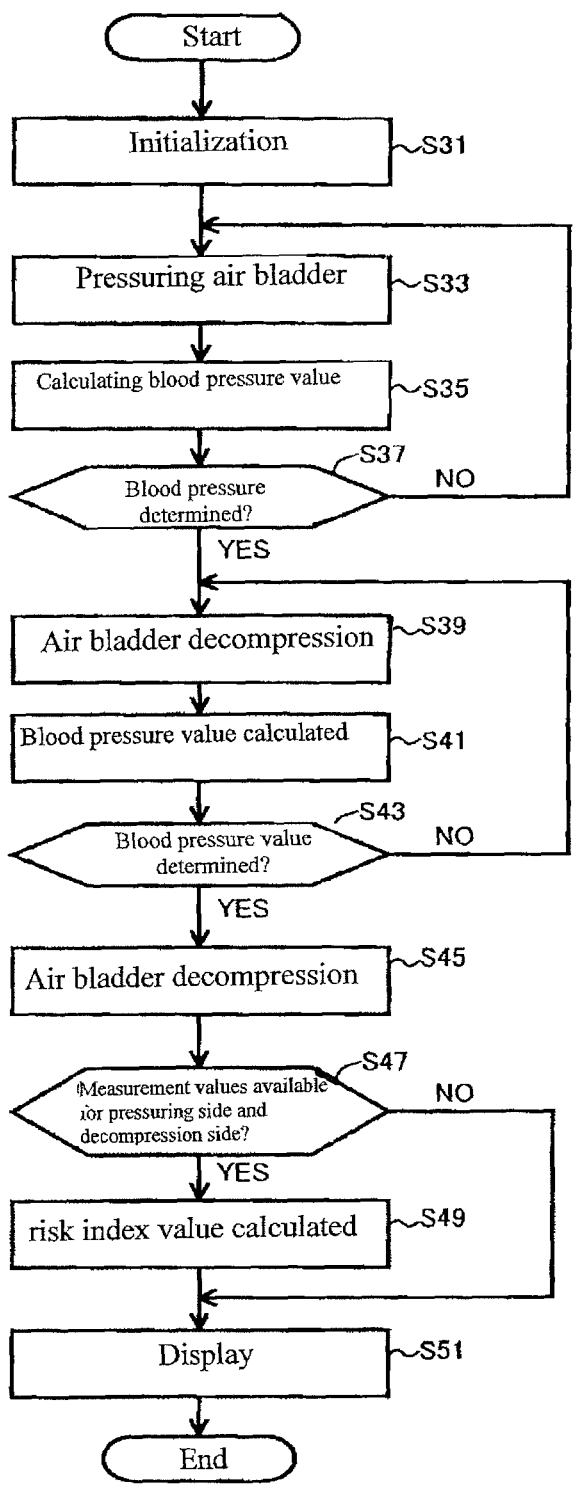
FIG. 10 is a flow chart illustrating an operation in the sphygmomanometer according to the second embodiment.

FIG. 10 is a flow chart showing the operation of the sphygmomanometer 1 of the second embodiment. The operations shown in the flow chart of FIG. 10 are also started when the switch 32 that is included in the operation part 3 is pressed. This operation is realized when CPU 40 reads the control program that is stored in the memory part 5B and controls each part shown in FIG. 5B.

Referring to FIG. 10, when the measurement operation is started, CPU 40, after each part is initialized at Step S31, outputs the control signal with respect to the drive circuit 26 and the drive circuit 27 at Step S33, closes the valve 22 and operates the pump 21, and then pressurizes the air bladder 13.

During the pressurization process, at Step S35, CPU 40 extracts a vibrational component according to the volume change of a convoluted artery due to the internal pressure of the air bladder 13, and calculates the blood pressure value by the predetermined calculation.

When the calculation of the blood pressure value is completed and the blood pressure value is determined (YES at Step S37), at Step 39, CPU 40 outputs the control signal to the drive circuit 26 and stops pressurizing, outputs the control signal to the drive circuit 27, and releases the valve 22 for the predetermined amount. Accordingly, the depressurization of the air bladder 13 starts. At the sphygmomanometer 1 of the that embodiment, after the blood pressure value is calculated during the pressurization process, the measurement ends and the air bladder 13 is rapidly depressurized. However, with the sphygmomanometer 1 of the second embodiment, the air bladder 13 is gradually depressurized in order to have a fluctuation speed that is adequate to the measurement in order to measure the blood pressure during the depressurization process.

Also, during the depressurization process, at Step S41, CPU 40 extracts the vibrational component according to the volume change of the convoluted artery due to the internal pressure of the air bladder 13, and calculates the blood pressure value by the predetermined calculation.

When calculation of the blood pressure value is completed, and the blood pressure value is determined, (YES at Step S43), at Step S45, CPU 40 outputs the control signal to the drive circuit 27, and releases the valve 22. By doing this, the air bladder 13 rapidly depressurizes.

Here, when the blood pressure measurement is successful for both the pressurization process and the depressurization process, and both measuring results are stored in the predetermined region of the memory 5B (YES at Step S47), at Step S49, CPU 40 calculates the index value r of risk of circulatory system disease by using the blood pressure value obtained during the depressurization process calculated at the Step S41. Here, r is calculated as the equation (3) shown below by using the systolic blood pressure value, SBPinf which is obtained by calculating the systolic blood pressure value that is obtained during the pressurization process and the systolic blood pressure value, SBPdef which is obtained by calculating the blood pressure value during the depressurization process.

$$r = SBPinf - SBPdef \quad \text{Equation (3)}$$

Moreover, r can be calculated as the equation (4) shown below by using its ratio without being limited by the difference of the blood pressure values.

$$r = (SBPinf/SBPdef) \quad \text{Equation (4),}$$

Moreover, similar to the equation (1) and the equation (2), r can be calculated as the below equations (5) and (6) by using the time difference t of the blood pressure measurement during the pressurization process and the blood pressure measurement during the depressurization process.

$$r = (SBPinf - SBPdef)/t \quad \text{Equation (5),}$$

$$r = (SBPinf/SBPdef)/t \quad \text{Equation (6).}$$

Then, at Step S51, CPU 40 executes a process in order to display the index value r of risk of the circulatory system disease that is calculated at Step S49 together with the blood pressure value that is measured at Steps S35 and S41 as a measurement result; and a series of the measuring operations are completed.

FIG. 11 shows the screen example that is displayed on the display part 4 by the processing at the above mentioned Step S51. As shown in FIG. 11, when the measurement is completed, together with both blood pressure values that are obtained at the pressurization process and the depressurization process, the index value r of risk of circulatory system disease is calculated using both blood pressures values. Moreover, either one of the blood pressure values may be displayed instead of both blood pressure values, or the average value of these may be displayed as shown in FIG. 1.

Moreover, in the flow chart shown in FIG. 10, whether regarding the measurement of the pressurization process or the measurement of the depressurization process, pressurizing or depressurizing will be performed until the blood pressure value is calculated. However, according to one or more embodiments of the present invention, the method may proceed even if due to an error, one or more of the measurements fail as the internal pressure of the air bladder 13 reaches the predetermined pressure. For example, if either one of the measurements fails, only the blood pressure may be displayed without performing the calculation of the index value. Moreover, in order to make the calculation of the index value possible, for example, a message stating such as "please measure again" may be stored in advance, and displayed together with the blood pressure value.

The sphygmomanometer 1 of the second embodiment is operated as stated, two measurement results can be obtained by the measuring operation in accordance with the first measurement, and the index value can be obtained based on that.

Moreover, in the above explanation, the index value of risk of circulatory system disease is calculated by using several measurement results within the predetermined period per one sphygmomanometer. However, according to one or more embodiments of the present invention, the index value may be calculated by using the measurement result of the calculation device when a function to output via the Internet or the like is loaded together with the information to specify the measurement date and time on the other calculation device such as a personal computer (PC) on the sphygmomanometer 1.

In this case, a program to execute the above mentioned operation to the calculating device can be provided. This kind of program can be recorded on a computer readable recording medium such as a floppy disk, Compact Disk-Read Only Memory (CD-ROM), Read Only Memory (ROM), Random Access Memory (RAM) and memory card, and can be provided as program products. Or, according to one or more embodiments of the present invention, the program can be recorded in a recording medium such as a hard disk that is built-in a computer. Moreover, this kind of program can be provided by downloading via network.

Further, the program according to one or more embodiments of the present invention can be a program to execute a process by calling a necessary module in the predetermined arrangement and the predetermined timing among the program modules that is provided as a part of the operation system (OS) of the computer. In this case, the above mentioned module is not included in the program itself and the process is executed with the cooperation of the OS. This kind of program that does not include the module can be included in the program according to one or more embodiments of the present invention.

Moreover, the program according to one or more embodiments of the present invention can be provided by integration into a part of the other program. In this case, the module that is included in the above mentioned other program is not included, and the process is executed with the cooperation of the other program. This kind of program that is integrated in the other program can be included in one or more embodiments of the present invention.

The provided program products can be installed in the program storing pan such as hard disk. Moreover, the program product includes the program itself and the recording medium in which the program is recorded.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An electronic sphygmomanometer comprising:
an air bladder;
a pressure sensor that detects an internal pressure change of the air bladder;
a processor that a measures a current measurement and at least one previous measurement of blood pressure of a person being examined based on the detected internal pressure change of the air bladder, the current measurement and the previous measurement are effected at a same portion of the person being examined, the processor comprising:
a judging part that judges whether to calculate an index value of risk of circulatory system disease of the person being examined based on the comparison of the current measurement and the previous measurement;
an index value calculating part that calculates the index value of risk of circulatory system disease of the person being examined based on:
the judging result of the judging part;
a difference between a blood pressure value of the person being examined obtained from the current measurement and a blood pressure value of the person being examined obtained from the previous measurement; and
an elapsed time between the current measurement and the previous measurement;
a memory that stores the at least one previous measurement of blood pressure of the person being examined together with a time information of the at least one previous measurement; and
a display that displays the calculated index value of risk of circulatory system disease of the person being examined and the current measured blood pressure.

2. The electronic sphygmomanometer according to claim 1, wherein the index value of risk of circulatory system disease is calculated by dividing the difference between the blood pressure value of the person being examined obtained from the current measurement and the blood pressure value of the person being examined obtained from the previous measurement by the elapsed time between the current measurement and the previous measurement.

3. The electronic sphygmomanometer according to claim 1, wherein the blood pressure value of the person being examined is systolic blood pressure obtained from each measurement.

4. The electronic sphygmomanometer according to claim 1,
wherein the processor measures the current measurement and the at least one previous measurement of blood pressure of the person being examined based on the detected internal pressure change of the air bladder during an inflating process of a cuff; and wherein the processor measures the current measurement and the at least one previous measurement of blood pressure of the person being examined based on the detected internal pressure change of the air bladder during a deflating process of the cuff that follows after the inflating process, wherein the index value of risk of circulatory system disease of the person being examined is calculated by dividing a difference of the blood pressure value obtained from the measurement at the inflating process and the blood pressure value obtained from the measurement at the deflating process by an elapsed time between the measurement at the inflating process and the measurement at the deflating process.

5. The electronic sphygmomanometer according to claim 1, further comprising means for inputting ID information of the person being examined.

6. A non-transitory computer readable medium having stored thereon a program that causes a CPU to execute a process of calculating an index value of risk of circulatory system disease of a person being examined, the program causing the CPU to execute a process comprising:

measuring a current and at least one previous measurement of blood pressure of the person being examined based on a change of internal pressure of an air bladder of a sphygmomanometer, wherein the current measurement and the previous measurement are effected at a same portion of the person being examined;

storing data of the at least one previous measurement of blood pressure value of the person being examined together with time information of the measurement in a memory;

retrieving stored data of the at least one previous measurement together with the time information;

judging whether to calculate the index value of risk of circulatory system disease of the person being examined based on a comparison of the current measurement and the previous measurement;

calculating the index value of risk of circulatory system disease for the person being examined by dividing a difference between the blood pressure value of the person being examined obtained from the current measurement and the blood pressure value of the person being examined obtained from the previous measurement, by an elapsed time between the current measurement and the previous measurement, wherein the calculating the index value of risk of circulatory system disease for the person being examined step depends on the result of the judging step.

7. The non-transitory computer readable medium according to claim 6, wherein the blood pressure of the person being examined is systolic blood pressure obtained from each measurement.

8. A method of calculating an index value of risk of circulatory system disease from blood pressure information, the method comprising:

measuring a current and at least one previous measurement of blood pressure of a person being examined based on a change of internal pressure of an air bladder of a sphygmomanometer, wherein the current measurement and the previous measurement are effected at a same portion of the person being examined;

retrieving stored data of the at least one previous measurement;

judging whether to calculate the index value of risk of circulatory system disease of the person being examined based on a comparison of the current measurement and the previous measurement; and dividing a difference between the current measurement and the previous measurement by an elapsed time between the current measurement and the previous measurement to obtain the index value of risk of circulatory system disease, wherein the dividing step depends on the result of the judging step.

* * * * *